United States Patent [19]

Van Caneghem

[11] Patent Number: 4,534,205
[45] Date of Patent: Aug. 13, 1985

[54] METHOD OF SHOCK TESTING ALUMINUM ALLOY WELDED JOINTS

[75] Inventor: René J. Van Caneghem, Elkton, Md.

[73] Assignee: The United States of America as represented by the Secretary of the Army, Washington, D.C.

[21] Appl. No.: 620,789

[22] Filed: Jun. 15, 1984

[51] Int. Cl.³ .............................................. G01N 3/30
[52] U.S. Cl. ........................................ 73/12; 73/799; 73/842; 73/844
[58] Field of Search ................... 73/12, 81, 78, 82, 87, 73/167, 799, 842, 844

[56] References Cited

U.S. PATENT DOCUMENTS

| | | | |
|---|---|---|---|
| 3,645,130 | 2/1972 | Million et al. | 73/799 |
| 3,872,709 | 3/1975 | Pagano | 73/12 |
| 4,044,599 | 8/1977 | Goldstein et al. | 73/12 |
| 4,418,563 | 12/1983 | Kaithoff | 73/12 |

Primary Examiner—Donald O. Woodiel
Attorney, Agent, or Firm—Anthony T. Lane; Robert P. Gibson; Saul Elbaum

[57] ABSTRACT

Aluminum alloy armor weld joints are ballistic shock tested by first separately determining the ballistic impact capability of the components to be joined by the weldment by firing a plate proofing projectile at 0° obliquity at each of said components at different striking velocities. The welded joint designs and welding procedures are then tested by firing the same projectile at the same angle at each of the components of the weldment so that the projectile impacts each component in the vicinity of the weld at a velocity comparable to the critical velocity of the component being impacted.

5 Claims, 6 Drawing Figures

METHOD OF SHOCK TESTING ALUMINUM ALLOY WELDED JOINTS

RIGHTS OF THE GOVERNMENT

The invention described herein may be manufactured, used and licensed by or for the United States Government without the payment to me of any royalty thereon.

BACKGROUND OF THE INVENTION

Prior to the present invention no military specification set forth any standardized procedure for testing or evaluating the ballistic shock absorption capability of aluminum alloy welded joints. Prior art ballistic tests of aluminum alloy armor weld joints have left the choice of test projectile type and caliber, impact velocity, impact obliquity, location of impact and allowable crack length to the discretion of the tester. Historically, the only tests considered reliable have been those conducted on 90° corner joints or on "H" plates wherein four coplanar plates are welded together with the welds forming the letter H. No method has heretofore been known or used for evaluating welding procedures or designs as applied to the welded joints of similar or dissimilar aluminum alloy armor components wherein the joint angles could be 0 degrees representing coplanar welded components, or either acute or obtuse angles between the components, and wherein the two welded armor plates may be of equal or unequal thickness. The present invention provides a novel and efficient method of testing and evaluating welds having any of the characteristics described.

SUMMARY OF THE INVENTION

The concept of the method of the present invention comprises subjecting each of the armor plate components, in the vicinity of weld joining the components, to a ballistic impact somewhat less than that which will cause long cracks or catastrophic failure of that component when separately tested for shock absorption capability. Thus the strength of the weld is tested in relation to the strength of the components forming the weld.

The methodology involves determining the critical striking velocity of all of the various thicknesses of the different alloys of the armor plates to be welded and tested. The critical velocity is that velocity below which only short cracks or no cracks can be expected and above which long cracks or catastrophic failure are likely when the plate is impacted with a standard plate proofing projectile. The welded joints of any combination of plate components welded at any angle is then tested with the same projectile fired at 0° obliquity at each of the plates at a point about 2 inches (or 5 cm) from the nearest point of the weld, at a striking velocity somewhat less than the aforementioned critical velocity of the plate being impacted.

It is thus an object of the invention to provide a novel and useful method of testing welding procedures as well as welding designs of welded aluminum alloy armor plates which is applicable to welded joints comprising plates of different thickness and/or different alloys joined at any angle.

Another object of the invention is to provide a method of simply and easily determining the ballistic shock absorption capability of the weldments of welded aluminum alloy armor plates relative to the ballistic shock absorption capability of the components of the weld.

These and other objects and advantages of the invention will become apparent from the following detailed description and the drawings.

DETAILED DESCRIPTION OF A PREFERRED EMBODIMENT

In accordance with one feature of the invention, the ballistic shock absorbing capability of welded joints of aluminum alloy armor is tested in relation to the strength of the components which are joined by the weld. Thus it is necessary to determine the strength of all of the various thicknesses of the different alloys of the armor plates which are to be welded. An armored vehicle known as the Infantry Fighting Vehicle/Combat Fighting Vehicle (IFV/CFV), presently under development by the U.S. Army, includes two types of aluminum alloy armor, known as 5083 and 7039, with the plates thereof welded together at various angles and with different thicknesses of the same or different alloys forming the welded components. The method of this invention was first applied to evaluating the ballistic shock absorbing capability of the different types of welds of these two aluminum alloys, and will be described in connection therewith.

Figure 1:
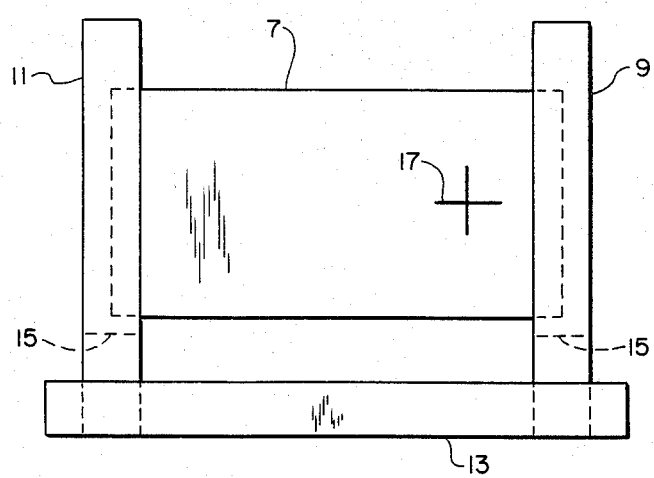
FIG. 1 shows a test stand for determining the critical striking velocities of armor plate.

The ballistic shock absorbing strength or capability of sample plates of these two alloys of various thicknesses was determined with a test setup depicted in FIG. 1. A rectangular armor plate 7 to be tested is mounted in the vertical plane in a test stand comprising a base 13 and two upright members 9 and 11, which include slots 15 on the inside thereof. The test plate 7 is dropped into the slots 15 and wedged in place with wooden wedges, not shown. The cross 17 is the intended impact point of a plate proofing projectile which is fired at 0° obliquity (or normal to the broad plate surface). The projectile used was the 75 mm, M1002A aluminum plate proofing projectile which is generally cylindrical shape approximately 75 mm in diameter and 20 cm long. The different striking velocities are obtained by varying the propellant charge of the cartridge case in which the proofing projectile is mounted.

The firing procedure was the normal up and down firing method commonly used in ballistic limit determinations. For example, if the first round fired caused little or no plate cracking, the next round was fired at a higher striking velocity. If this round caused excessive cracking the velocity of the next round was adjusted downward to cause less cracking, etc. This procedure was followed until an equal number of impacts causing little damage (i.e. no cracks or cracks less than 12 inches long) and an equal number of impacts causing excessive damage (i.e. cracks longer than 12 inches or catastrophic failure), were attained within a velocity spread of 125 ft/sec (38 m/s). Four or six rounds were used to assure reproducibility of results. Propellant charges were adjusted upward or downward by an amount estimated to produce a velocity change of about 50 ft/sec. The average of all of these striking velocities represents the critical striking velocity. This velocity is sometimes called the $V_{50}$ velocity and striking velocities below this figure will normally not cause long cracks or catastrophic failure, whereas velocities above this figure likely will cause such damage.

Figure 2:
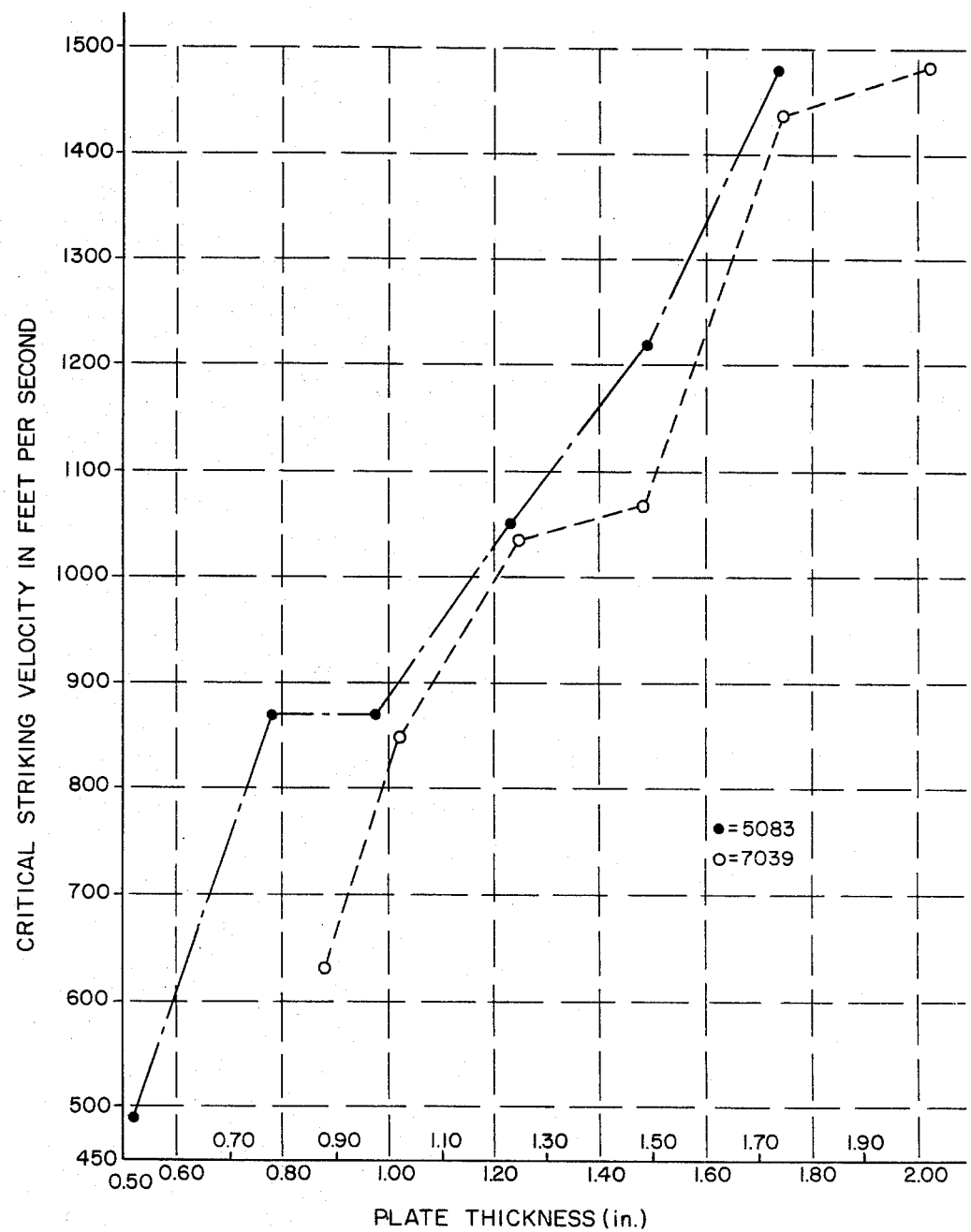
FIG. 2 is a graph of the critical striking velocities of different thicknesses of aluminum armor plate of two different alloys.

FIG. 2 is a plot of the critical striking velocities vs. thickness so obtained for plates of the two aluminum alloys 5083 and 7039.

In accordance with the invention, the strength and the design of welds are evaluated by separately impacting each of the components of the weld once within approximately 2 inches (or 5 cm) of the edge of the weld with the same plate proofing projectile used to determine the aforementioned critical striking velocities, and at a 0° angle of obliquity, with the welded components suitably supported. The 17 different welded-joint designs used in the aforementioned IFV/CFV were shock tested in this manner and the results evaluated, with the striking velocities ranging from the critical velocity of the weldment component down to 100 feet/sec. below the critical velocity. An evaluation of the results of these tests led to the conclusion that the striking velocity of the proofing projectile should be approximately 60 feet/sec. below the critical velocity of the weldment component for the two aluminum alloys involved with the tests described. The absence of any cracks longer than 12 inches in the weldment after impact at this velocity on each of the two components within 2 inches of the weld edge indicates a good weld design as well as a good welding procedure.

Tables I and II below list the striking velocities for the different thicknesses of the aluminum alloy plates for the alloys 5083 and 7039, respectively. These striking velocities are 60 feet/sec. less than the critical velocities shown in the graph of FIG. 2.

TABLE I (Alloy 5083)

| Thickness (In.) | Striking Velocity (fps) |
|---|---|
| 0.625 | 620 |
| 0.750 | 790 |
| 0.875 | 815 |
| 1.000 | 825 |
| 1.125 | 920 |
| 1.250 | 1005 |
| 1.375 | 1085 |
| 1.500 | 1175 |
| 1.625 | 1330 |
| 1.750 | 1440 |

TABLE II (Alloy 7039)

| Thickness (In.) | Striking Velocity (fps) |
|---|---|
| 0.875 | 620 |
| 1.000 | 775 |
| 1.125 | 890 |
| 1.250 | 985 |
| 1.375 | 1000 |
| 1.500 | 1015 |
| 1.625 | 1260 |
| 1.750 | 1390 |
| 1.875 | 1410 |
| 2.000 | 1430 |

Figure 3A:
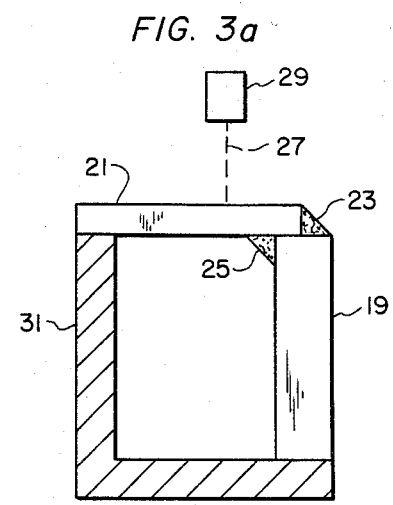
FIGS. 3a and 3b show a pair of aluminum alloy plates welded at right angles being given a ballistic shock test.
Figure 3B:
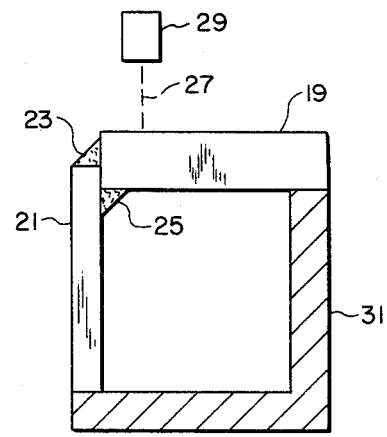

FIGS. 3a and 3b represent top views of the same two aluminum alloy plates 19 and 21 welded at right angles and undergoing ballistic impact tests in accordance with the method of the present invention. The joint is welded at the outside thereof as indicated by weld 23 and also on the inside as indicated by weld 25. The two components of this particular joint were of the same alloy, namely 5083, with the component 19 being thicker than component 21, as indicated. FIG. 3a shows the component 21 about to be impacted by a proofing projectile 29 which follows the dashed line path 27 to strike the component in the vicinity of weld 25, within approximately 2 inches thereof, at a striking velocity as indicated in Table I for the thickness of that component. The hatched area 31 represents a suitable brace or test stand against which the component being tested is placed. FIG. 3b shows the thicker component 19 placed against brace 31 and about to be impacted by a similar proofing projectile 29 in the vicinity of weld 25.

Figure 4:
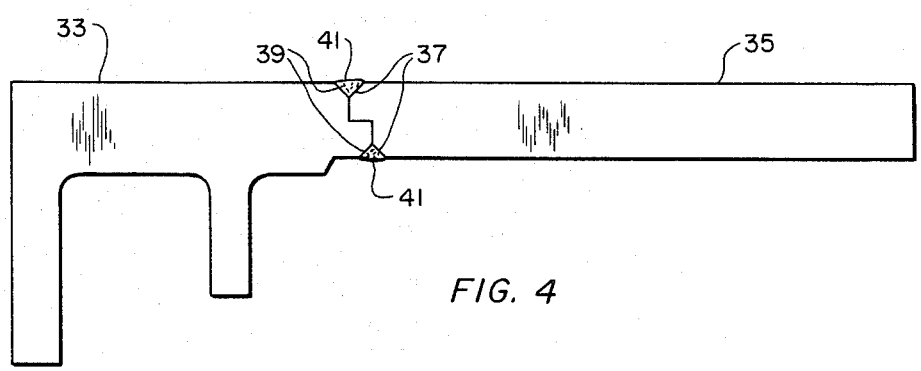

FIG. 4 shows how an aluminum alloy extrusion 23, which may be of alloy 5083, may be butt welded to an aluminum alloy armor plate 35 which may be of alloy 7039. The ends of these components at the joint have complementary stepped shapes, as shown, with bevels 39 on component 33 and similar bevels 37 on the mating surfaces of the other component. These four bevels form two V-shaped grooves when the components are joined end-to-end as shown in FIG. 4. These grooves form troughs for receiving the welding material 41.

Figure 5:
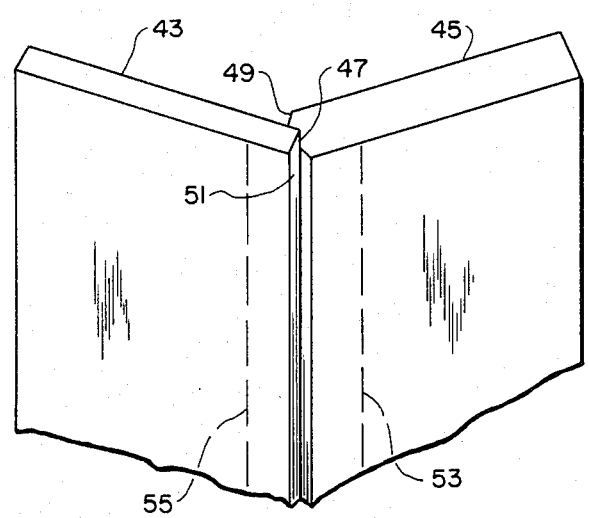
FIGS. 4 and 5 show other types of welded plate joints which can be tested in accordance with the present invention.

FIG. 5 shows a pair of armor plates welded at an obtuse angle with one component, 43, thinner than the other component, 45. The component 45 has a V-shaped groove 47 along the joint to be welded and the corner of component 43 fits into this groove to form two V-shaped troughs 49 and 51, one on the inside of the joint and the other on the outside, as illustrated. These troughs may be filled with welding material. The test projectile may be directed anywhere along the dashed lines 53 or 55 which are approximately 2 inches from the edge of the welds. The test projectile can impact on either side of the welded plates, as long as the test specimen is suitably braced. In general, the proofing projectile should strike the armor plates on the sides thereof from which the threat would come in the field.

Unusual designs of welded joints such as those illustrated in FIGS. 4 and 5 can be evaluated for impact strength with the present method. Also, proven or conventional weld designs can be tested on a sampling basis for quality control purposes during production, using this novel testing method.

I wish it to be understood that I do not desire to be limited to the exact details of construction shown and described, for obvious modifications can be made by a person skilled in the art.

I claim:

1. A method of shock testing the welded joints of aluminum alloy armor plate wherein the components of said welded joints may be of diverse thickness and different alloys, comprising the steps of; determining with a standard plate proofing projectile at 0 degrees obliquity the critical velocity of each of said diverse thicknesses of said armor plates of each of said different alloys, said critical velocity being defined as that velocity below which either no cracks or cracks less than 12 inches long can be expected and above which longer cracks or catastrophic failure can be expected, then testing said welded joints by separately impacting each of the said components joined by said joint in the vicinity of said joint with the said standard plate proofing projectile at 0 degree obliquity at a striking velocity less than said critical velocity.

2. The method of claim 1 wherein said striking velocity is approximately 60 feet/sec. less than the said critical velocity of each of said components being impacted and the impact point on each of said components is approximately 2 inches from the edge of the weld forming said joint.

3. A novel method of testing and evaluating welding procedures and weld joint designs of aluminum armor plate, comprising the steps of; separately determining the ballistic impact capability of each of the components of a weldment by firing a plate proofing projectile at 0 degrees obliquity at each of said components, then testing and evaluating the impact strength of a weldment of any pair of said components by firing the same plate proofing projectile at the same angle at each of said components within 2 inches of the weldment joining said components at a striking velocity approximately the same as that above which the component being impacted would be likely to suffer serious damage.

4. The method of shock testing welded joints of aluminum alloy armor plates which may have different thicknesses and/or comprise different alloys, comprising the steps of; determining the critical velocity of each of said plates to be welded, said critical velocity being that velocity of a standard plate proofing projectile below which only short cracks or no cracks are likely to result if said projectile impacts the said plates at normal incidence, then testing welded joints comprising any pair of said plates by firing the said plate proofing projectile at each of said plates at normal incidence and at a striking velocity comparable to the said critical velocity of the plate being impacted, and in the vicinity of the weldment joining said pairs of plates.

5. The method of claim 4 wherein said striking velocity is approximately 60 feet/sec. less than said critical velocity and said vicinity of said weldment is approximately 2 inches from said weldment.

* * * * *